(12) United States Patent
Levitt

(10) Patent No.: US 8,871,801 B2
(45) Date of Patent: Oct. 28, 2014

(54) METHOD OF TREATING ACQUIRED PERFORATING DERMATOSIS WITH CANTHARIDIN

(76) Inventor: Jacob Levitt, New York, NY (US)

( * ) Notice: Subject to any disclaimer, the term of this patent is extended or adjusted under 35 U.S.C. 154(b) by 195 days.

(21) Appl. No.: 13/507,771

(22) Filed: Jul. 27, 2012

(65) Prior Publication Data

US 2013/0197075 A1 Aug. 1, 2013

Related U.S. Application Data

(60) Provisional application No. 61/574,358, filed on Aug. 1, 2011.

(51) Int. Cl.
*A61K 31/34* (2006.01)

(52) U.S. Cl.
CPC ........................ *A61K 31/34* (2013.01)
USPC .......................... 514/468; 514/461

(58) Field of Classification Search
CPC ........................................ A61K 31/34
USPC ................ 549/231, 237; 514/449, 461, 468
See application file for complete search history.

(56) References Cited

PUBLICATIONS

Lin et al (2012): STN International Hcaplus database, Columbus (OH), accession No. :2012:92821.*

* cited by examiner

*Primary Examiner* — Golam M M Shameem
(74) *Attorney, Agent, or Firm* — Ohlandt, Greeley, Ruggiero & Perle, LLP

(57) ABSTRACT

A method of treating acquired perforating dermatosis. The method has the step of applying an amount of cantharidin to an area of skin in need of treatment thereof.

6 Claims, 8 Drawing Sheets

(8 of 8 Drawing Sheet(s) Filed in Color)

METHOD OF TREATING ACQUIRED PERFORATING DERMATOSIS WITH CANTHARIDIN

CROSS-REFERENCE TO A RELATED APPLICATION

The present application claims priority based upon U.S. Provisional Patent Application No. 61/574,358, filed Aug. 1, 2011, the disclosure of which is incorporated herein in its entirety.

BACKGROUND OF THE DISCLOSURE

1. Field of the Disclosure

The present disclosure relates to a method for treating acquired perforating dermatosis. (APD).

2. Description of the Related Art

Acquired perforating dermatosis (APD) describes a group of disorders associated with transepidermal elimination of collagen, elastic tissue, and/or necrotic connective tissue. The disease is acquired in adulthood. Persons having APD typically have certain systemic diseases such as renal failure and diabetes mellitus. The classic four presentations of perforating dermatosis are Kyrle's disease (KD), reactive perforating collagenosis (RPC), perforating folliculitis (PF), and elastosis perforans serpiginosa (EPS). APD can histologically resemble KD, RPC, PF and occasionally EPS. A significant percentage of dialysis patients also present with APD—11% in the British medical literature and ranging from 4.5% to 10% in the American medical literature. APD has also been reported in association with other systemic disorders including lymphoma, pancreas carcinoma, hypothyroidism, hyperparathyroidism, myelodysplastic syndrome, and AIDS.

APD and related disorders are disclosed and described in the literature at the following: (A) Lebwohl M, Berth-Jones, J., Heymann W. R., Coulson, I., *Treatment of Skin Disease: Comprehensive Therapeutic Strategies,* 3rd ed. Philadelphia: Saunders Elsevier 2010; (B) Kawakami T, Saito R., *Acquired Reactive Perforating Collagenosis Associated with Diabetes Mellitus: Eight Cases that Meet Faver's Criteria*, Br J Dermatol, March 1999; 140(3): 521-524; (C) Morton C A, Henderson I S, Jones M C, Lowe J G., *Acquired Perforating Dermatosis in a British Dialysis Population*, Br J Dermatol, November 1996; 135(5): 671-677; (D) Satti M B, Aref A H, Raddadi A A, Al-Ghamdi F A, *Acquired Reactive Perforating Collagenosis: A Clinicopathologic Study of 15 Cases from Saudi Arabia,* J Eur Acad Dermatol Venereol,. Feburary 2010; 24(2): 223-227; (E) Rapini R P, Herbert A A, Drucker C R, *Acquired Perforating Dermatosis. Evidence for Combined Transepidermal Elimination of both Collagen and Elastic Fibers,* Arch Dermatol, August 1989; 125(8): 1074-1078; (F) Abe R, Murase S, Nomura Y, et al., *Acquired Perforating Dermatosis Appearing as Elastosis Perforans Serpiginosa and Perforating Folliculitis,* Clin Exp Dermatol, August 2008; 33(5): 653-654; (G) Haftek M, Euvrard S, Kanitakis J, Delawari E, Schmitt D., *Acquired Perforating Dermatosis of Diabetes Mellitus and Renal Failure: Further Ultrastructural Clues to its Pathogenesis,* J Cutan Pathol, August 1993; 20(4): 350-355; (H) Hood A F, Hardegen G L, Zarate A R, Nigra T P, Gelfand M C, *Kyrle's Disease in Patients with Chronic Renal Failure,* Arch Dermatol, February 1982; 118(2): 85-88; (I) Hurwitz R M, Melton M E, Creech F T, 3rd, Weiss J, Handt A., *Perforating Folliculitis in Association with Hemodialysis,* Am J Dermatopathol, April 1982; 4(2): 101-108; (J) Patterson J W, *The Perforating Disorders*, J Am Acad Dermatol, April 1984; 10(4): 561-581; (K) Saray Y, Seckin D, Bilezikci B, *Acquired Perforating Dermatosis: Clinicopathological Features in Twenty-Two Cases,* J Eur Acad Dermatol Venereol, July 2006; 20(6): 679-688; (L) Mehregan A H, Coskey R J, *Perforating folliculitis,* Arch Dermatol, April 1968; 97(4): 394-399; (M) Cochran R J, Tucker S B, Wilkin J K, *Reactive Perforating Collagenosis of Diabetes Mellitus and Renal Failure,* Cutis, January 1983; 31(1): 55-58; (N) Bilezikci B, Seckin D, Demirhan B, *Acquired Perforating Dermatosis in Patients with Chronic Renal Failure: A Possible Pathogenetic Role for Fibronectin,* J Eur Acad Dermatol Venereol, March 2003; 17(2): 230-232; (O) Moed L, Shwayder T A, Chang M W, *Cantharidin Revisited: A Blistering Defense of an Ancient Medicine,* Arch Dermatol., October 2001; 137(10): 1357-1360; and (P) Pierard-Franchimont C, Pierard G E. Cantharidin-Induced Acantholysis, Am J Dermatopathol, October 1988; 10(5): 419-423.

The pathophysiology behind APD is unclear. It has been postulated that mechanical trauma, such as chronic rubbing from pruritus, diabetes mellitus, and renal failure, causes epithelial hyperplasia, follicular hyperkeratosis, and degeneration of connective tissue in the dermis. Diabetic vasculopathy and oxidation injury may also lead to dermal necrosis. Some APD patients on peritoneal or hemodialysis have developed lesions upon initiating dialysis. The role of increased serum fibronectin in patients with diabetes mellitus and uremia may also be a factor as increased fibronectin has been found in the skin at the sites of perforating lesions.

Many treatments have been proposed for treating APD. Success has varied. In general, treatment efforts have been unsatisfactory, and definitive resolution of existing lesions has been difficult to achieve.

First-line therapies for perforating dermatosis include tretinoin 0.1% (topical), broadband UVB (ultraviolet B), and narrowband UVB. Second-line therapies include allopurinol, PUVA (psoralens +ultraviolet A), and acitretin. Third-line therapies include 0.5% phenol with 10% glycerine in sorbolene, doxycycline (oral), surgical debridement, and transcutaneous electrical nerve stimulation. Topical steroids have also been employed.

It would be desirable to have an effective treatment for APD. It would also be desirable to have a treatment that is applied topically and is effective with respect to reduction/amelioration of symptoms and clearance of lesions.

SUMMARY OF THE DISCLOSURE

According to the present disclosure, there is provided a method of treating acquired perforating dermatosis, comprising applying an amount of cantharidin to an area of skin in need of treatment thereof.

BRIEF DESCRIPTION OF THE DRAWINGS

The patent or application file contains at least one drawing executed in color. Copies of the patent or patent application publication with color drawing(s) will b provided by the Office upon request and payment of the necessary fee.

DETAILED DESCRIPTION OF THE DISCLOSURE

Cantharidin is a topical vesicant and keratolytic agent. It has been used in dermatologic therapy to treat molluscum contagiosum and warts. Topical cantharidin treatment can cause blister formation within 24 to 48 hours. The blistering effect may be increased by lengthening the contact time or by increasing percutanebus absorption by applying a nonporous tape.

Although not bound by any theory, application of cantharidin to the skin may induce acantholysis of the suprabasal level, the entire stratum spinosum, and the epithelial adnexa down to the level of the sebaceous glands. The process results in blister formation.

Although not bound by any theory, when cantharidin is applied to APD lesions, it is believed to deeply penetrate and impact the epidermis all the way down to the hair follicles, which leads to the loosening of the central keratotic plug. When a blister roof is removed, the keratotic core can be extracted with the blister roof. Although cantharidin may require application to individual lesions, it provides an effective, safe, non-scarring topical modality for treatment of APD lesions.

In the method of the present disclosure, an amount of cantharidin is applied to human skin in need of treatment thereof for APD lesions. Preferably, the amount of cantharidin applied to the skin is effective to provide symptomatic relief to the patient. Symptomatic relief can include reduction or diminution of pruritus. Further preferably, the amount of cantharidin applied to the skin is effective to reduce or diminish the appearance or incidence of lesions. thereon.

Cantharidin has a general formula of $C_{10}H_{12}O_4$, a molecular weight of 196.2, and the following structure:

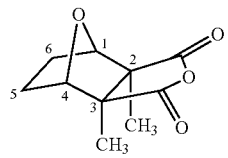

Cantharidin is preferably applied to the skin in the form of a composition with a vehicle. The vehicle will typically take the form of a liquid or a semi-solid. Cantharidin may be applied by hand or with an applicator. Useful examples of composition forms include a lotion, cream, solution, wax, or ointment. Cantharidin is preferably present in the composition at from about 0.1 wt % to about 10 wt % and more preferably about 0.5 wt % to about 5 wt % based on the total weight of the composition. Cantharidin may also be delivered, if desired, transdermally via a patch.

Ingredients useful in forming the vehicle for the composition include water, polyhydric and monohydric alcohols, organic waxes, organic oils, and the like. Examples of organic waxes and oils can include fatty acids, fatty esters, and fatty alcohols.

If desired, the composition may further contain other dermatological actives or excipients. Useful actives and excipients include keratolytic agents, colorants, diluents, exfoliants, conditioners, humectants, antimicrobials, and preservatives.

EXAMPLE

Figure 1:
FIG. 1 is a photographic image of a leg with acquired perforating dermatosis prior to treatment (pre-treatment).
Figure 6:
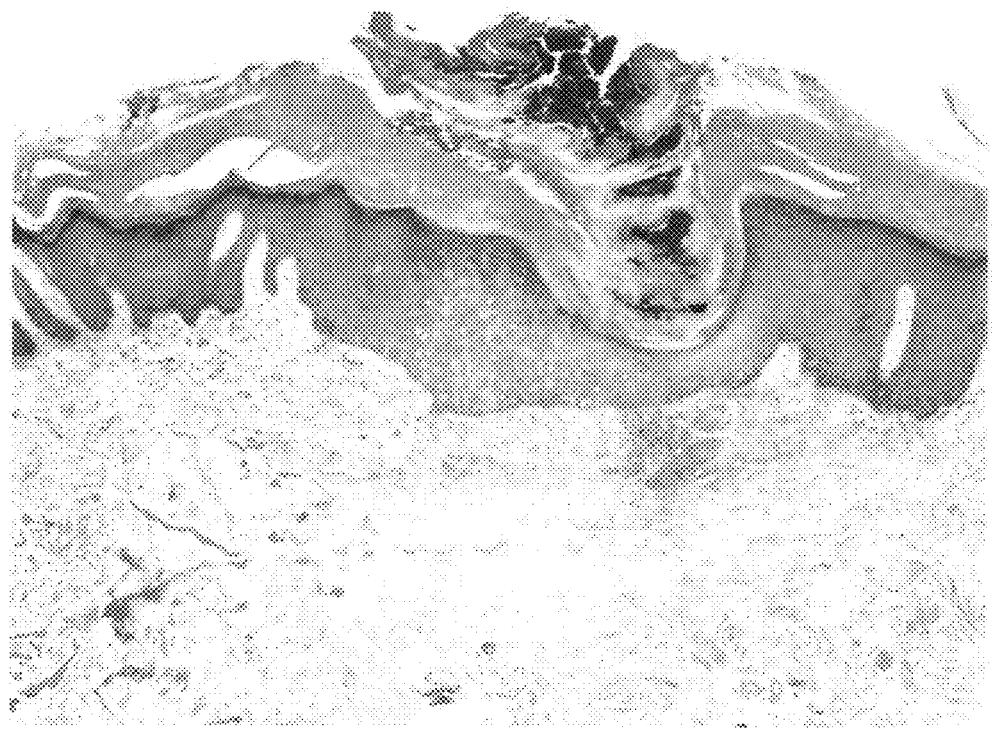
FIG. 6 is a photographic image of a cross-section of epidermis of the leg depicting an invagination filled with a large column of orthokeratotic and parakeratotic keratin (H and E, 10×).

A 65 year old woman presented a six-month history of pruritic, hyperpigmented papules with central, hyperkeratotic plugs of bilateral lower extremities (FIG. 1). The trunk, head, upper extremities, volar surfaces and mucous membranes were spared. Her past medical history was significant for chronic renal failure treated for the past four years with peritoneal dialysis, a 30-year history of insulin-dependent diabetes mellitus, hypercholesterolemia, hypertension, coronary artery bypass, hypothyroidism, and hyperparathyroidism. There was no family history of similar skin lesions. A biopsy from a lesion on the left leg revealed keratotic plugs filled with a laminated orthokeratotic and parakeratotic keratin and debris. Beneath the plug, the epidermis was thinned and the dermis showed a neutrophilic infiltrate and foci of fibrosis (FIG. 6). Trichome staining showed rare focal collagen extruding through the base. The surrounding skin showed features of lichen simplex chronicus. The clinical and histopathologic features supported the diagnosis of an acquired perforating disorder associated with renal disease.

Over the next six months, the patient was treated with intralesional triamcinolone at 10 mg/cc, topical clobetasol, diflorasone, tacrolimus, tazarotene and ammonium lactate. She declined narrowband UVB phototherapy. She was also given oral hydroxine and fexofenadine for her pruritus.

While a therapy of fexofenadine 60 g bid, ammonium lactate 12% cream bid, and tazarotene 0.1% cream qd were continued, cantharidin at 0.7 wt % (Canthacur® Pharmascience Inc., Montreal, Canada) was applied to lesions on the right medial calf. Cantharidin was applied for eight hours under occlusion. The vehicle was a solution containing cantharidin 0.7 wt % in acetone, castor oil, collodion, ethoxyethanol, ethyl cellulose, and polyoxyethylene octyl phenol. "bid" means twice per day. "qd" means once per day.

Figure 2:
FIG. 2 is a photographic image of the leg with acquired perforating dermatosis of the leg seven days after application of cantharidin, before debridement (pre-debridement).
Figure 3:
FIG. 3 is a photographic image of a close-up of a debrided papule after cantharidin treatment. The image is an inset taken from FIG. 2 at the position indicated in white in FIG. 1.
Figure 4:
FIG. 4 is a photographic image of the leg with acquired perforating dermatosis two months after treatment and after debridement.
Figure 7:
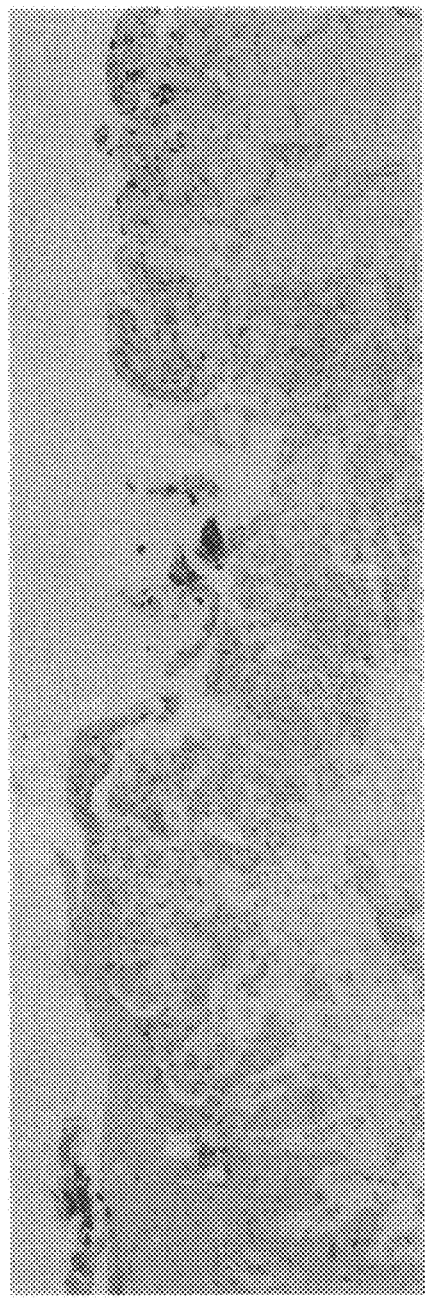
FIG. 7 is a photographic image of a subepidermal bulla with detachment of the epidermis, the dermis, and foci of dyshesion and necrosis (H and E, 10×).
Figure 8:
FIG. 8 is a photographic image of the leg one week after treatment showing perforating material attached to a blister roof.

The film was then occluded using Blenderm® tape, which was kept on for 8 hours before it was washed off. Within 2 days, multiple bullae formed at the sites of cantharidin application (FIG. 2). There was vesicle formation at site of cantharidin application. The patient reported mild pain at these sites for the first 2 days. A week after application, a biopsy of the blistered lesion was taken. The biopsy of the lesion with the blister showed focal acantholysis and scattered necrotic keratinocytes (FIG. 7). The blister roofs were then removed by paring them with a 15-blade at the edge of the lesion to find the blister plane and then lifting upwards. Surprisingly, the perforating material was attached to each blister roof (FIG. 8) resulting in complete clearance with residual hyperpigmentation (FIG. 4). The lichenified papules and hyperkeratotic cores were no longer present and the leg was smooth.

Figure 5:
FIG. 5 is a photographic image of the leg with acquired perforating dermatosis five months after treatment.

Pruritus was resolved in the treated lesions. Cantharidin was subsequently applied under Tegaderm® dressing (3M Corp.) occlusion to multiple lesions of both legs. While application was somewhat tedious, treatment was effective in most lesions. In a five-month follow up, the patient reported no pruritus on the treated lesions. Treated lesions were smooth. A few new lesions formed (FIG. 5). Cantharidin provides symptomatic relief but may not prevent the formation of new lesions.

Other teachings to the treatment of APD with cantharidin are disclosed in *Treatment of Acquired Perforating Dermatosis With Cantharidin*, Wong J., Phelps R., and Levitt J., Arch Dermatol, vol. 148 (No. 2), February 2012, which is incorporated herein by reference in its entirety.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

What is claimed is:

1. A method of treating acquired perforating dermatosis, comprising applying cantharidin to an area of skin in need of treatment thereof is an amount effective to provide symptomatic relief.

2. The method of claim 1, wherein the amount of cantharidin applied to the skin is effective to reduce or diminish the appearance or incidence of lesions.

3. The method of claim 1, wherein the cantharidin is applied in a composition along with a liquid vehicle or semi-solid vehicle.

4. The method of claim 3, wherein the vehicle is a semi-solid vehicle in the form of a cream.

5. The method of claim 1, wherein the cantharidin is present in the composition at from about 0.1 wt % to about 10 wt % based on the total weight of the composition.

6. The method of claim 1, wherein the cantharidin is present in the composition at from about 0.5 wt % to about 5 wt % based on the total weight of the composition.

* * * * *